United States Patent [19]
Bretler et al.

[11] Patent Number: 6,025,170
[45] Date of Patent: Feb. 15, 2000

[54] PROCESS FOR THE BIOTECHNOLOGICAL PRODUCTION OF δ-DECALACTONE AND δ-DODECALACTONE

[75] Inventors: Gil Bretler, Geneva; Christopher Dean, Grand-Lancy, both of Switzerland

[73] Assignee: Firmenich SA, Geneva, Switzerland

[21] Appl. No.: 09/138,897

[22] Filed: Aug. 24, 1998

[30] Foreign Application Priority Data

Aug. 27, 1997 [CH] Switzerland ............................. 2001/97

[51] Int. Cl.⁷ .................................................... C12P 17/06
[52] U.S. Cl. .......................... 435/125; 435/252.7; 435/842
[58] Field of Search ................................ 435/252.7, 125, 435/842

[56] References Cited

U.S. PATENT DOCUMENTS 5,128,261  7/1992  Maria de Laat et al. .............. 435/255
5,527,693  6/1996  Cardillo et al. ......................... 435/125
5,763,233  6/1998  Gocho et al. ........................... 435/125

FOREIGN PATENT DOCUMENTS 0 409 321 A1  1/1991  European Pat. Off. .
0 425 001 B1  5/1991  European Pat. Off. .
0 577 463 A2  1/1994  European Pat. Off. .

*Primary Examiner*—Herbert J. Lilling
*Attorney, Agent, or Firm*—Pennie & Edmonds LLP

[57] ABSTRACT

The invention describes a process for the preparation of δ-decalactone or δ-dodecalactone by the hydrogenation of 2-decen-5-olide and 2-dodecen-5-olide, or a derivative therof, by a bacteria capable of effecting said hydrogenation, preferably by a bacteria of the Clostridium genus. In an embodiment of the invention, 5-hydroxy-2-decenoic acid or 5-hydroxy-2-dodecenoic acid is used as substrate in the hydrogenation reaction.

10 Claims, No Drawings

PROCESS FOR THE BIOTECHNOLOGICAL PRODUCTION OF δ-DECALACTONE AND δ-DODECALACTONE

BRIEF DESCRIPTION OF THE INVENTION

The present invention relates to the field of biotechnology. It relates, more particularly, to a novel process for the preparation of δ-decalactone and δ-dodecalctone by hydrogenation of the corresponding unsaturated lactones or a derivative thereof by using bacteriae, in particular bacteriae belonging to the Clostridium genus.

BACKGROUND OF THE INVENTION

δ-Decalactone and δ-dodecalctone are highly appreciated flavoring compounds. They occur, in low quantities, in milk products, like butter, and they bring about an important contribution to the typical taste of these products. As a consequence of their low natural occurrence and their highly appreciated organoleptic characteristics, which are in particular searched for to confer the natural taste of butter and other milk products to margarine and yoghurt, there exists a strong need for processes capable of providing industrial quantities of these lactones, and in a quality which is in conformity with the legislations relative to food products.

The prior art describes processes for the production of these lactones, either by organic synthesis or by biotechnological processes. In the context of the present invention, one can cite three references disclosing the biotechnological preparation of δ-decalactone and δ-dodecalctone.

The process described in European patent application EP-A-409 321 consists of a β-oxidation of hydroxy fatty acids which are found in nature in form of their esters in the roots or the tubers of certain plants, like Ipomoea and Convolvulus. The use of several yeasts, fungi and bacteriae is described for effecting the β-oxidation, the preferred microorganisms belonging to the *Saccharomyces cerevisiae* species. The hydroxy acids obtained are then transformed into δ-decalactone or δ-dodecalctone.

Two other references describe the use of 2-decen-5-olide or, respectively, 2-dodecen-5-olide, as substrate. Said lactones can be isolated from the bark oil of the tropical *Cryptocarya massoia* tree, and their hydrogenation results in the desired saturated lactones.

European patent application EP-A-425 001 discloses the preparation of δ-decalactone and δ-dodecalctone by a hydrogenation reaction using certain yeasts, the most preferred belonging to the species *Saccharomyces cerevisiae*.

Likewise, European patent application EP-A-577 463 describes the hydrogenation of 2-decen-5-olide and 2-dodecen-5-olide to δ-decalactone and δ-dodecalctone, but there are used microorganisms different from those used in the above-cited application. The best results are again obtained with a yeast belonging to the Saccharomyces genus, in particular *Saccharomyces delbrueckii*.

It should be mentioned that the processes mentioned beforehand have the disadvantage that a low concentration of the final product is obtained, in the range of about 1.5 g/l, and have an extremely low volumetric productivity, comprised between about 0.01 and 0.09 g/lh.

DESCRIPTION OF THE INVENTION

Now, we have discovered a process for the preparation of δ-decalactone or δ-dodecalctone allowing to produce the said lactones in high quantities and with a higher productivity. Said process comprises the hydrogenation of 2-decen-5-olide or 2-dodecen-5-olide, or a derivative thereof, by a bacteria capable of effecting said hydrogenation. According to a preferred embodiment, said bacteria is an anaerobic bacteria, in particular of the Clostridium genus.

The processes known in the prior art are carried out under aerobic conditions. In the preferred embodiment of the invention, we use anaerobic bacteriae, and the hydrogenation reaction is carried out under conditions excluding oxygen. The hydrogenation reaction of unsaturated carboxylic acids under anaerobic conditions, using certain Clostridium strains, was studied by Simon et al. [see Angew. Chem. Int. Ed. 24 (1985), p. 539]. The same author could identify, in certain strains of the Clostridium genus, the 2-enoate-reductase enzyme, to which he attributed the found activity, e.g. to catalyze the hydrogenation of carboxylic acids unsaturated in α, β position. However, there is no mention in this prior art of any usefulness of such bacteria for converting the substrates of the present invention.

Bacteriae belonging to the Clostridium genus turned out to be an appropriate microbial catalyst for the hydrogenation of unsaturated lactones according to the present invention. As examples for said bacteria species, there are cited *Clostridium tyrobutyricum, Clostridium pasteurianium, Clostridium beujerincki, Clostridium acetobutylicum, Clostridium oceanium, Clostridium sticklandii* and *Clostridium thermobutyricum*.

From the species cited beforehand, it is preferred to use the strains *Clostridium tyrobutyricum* I-776, available from Institut Pasteur, Paris, France; *Clostridium tyrobutyricum* I-775, available from Institut Pasteur, Paris, France; *Clostridium tyrobutyricum* CNR2 556, available from Institut Pasteur, Paris, France; *Clostridium pasteurianium* DSM 525, available from Deutsche Sammlung von Mikroorganismen und Zellkulturen, Braunschwig, Germany; *Clostridium beijerinchi* DSM 6422, available from Deutsche Sammlung von Mikroorganismen und Zellkulturen, Braunschwigz, Germany; *Clostridium autobutylicum* DSM 792, available from Deutsche Sammlung von Mikroorganismen und Zellkulturen, Braunschwig, Germany.

In one embodiment of the invention, 2-decen-5-olide and 2-dodecen-5-olide are used as substrates in the hydrogenation reaction with an appropriate bacteria. In a further embodiment of the invention, 5-hydroxy-2-decanoic acid or 5-hydroxy-2-dodecanoic acid are used as substrate in the process of the invention, generally in the form of its salts.

We have found that, depending on the reaction conditions, e.g. the pH and the bacteriae used for a given hydrogenation reaction, it may be preferred to use the lactone as such or the salt of the corresponding acid as substrate upon which the bacteriae act.

The salts of the hydroxy acids can be obtained from 2-decen-5-olide or 2-dodecen-5-olide by the action of an appropriate base. As an alternative, an enzyme, for example a lipase, can be used for the purpose of opening the lactone cycle. To this end, also other enzymes are appropriate, and these are known to a person skilled in the art.

It is also possible to use as a substrate an appropriate ester of the α,β-unsaturated 5-hydroxy acid, for example an ester of a $C_1$- to $C_4$-alcohol. Such esters are in general obtained by transesterification. Appropriate esterification methods are known to a person skilled in the art, which methods comprise, for example, the chemical esterification (using, for example, the respective alcohol and an acid catalyst) and the biotechnological esterification (using an enzyme, for example a lipase) of either the 2-decen-5-olide or 2-dodecen-5-olide or the salt of the corresponding acid.

The hydrogenation reaction of the 2-decen-5-olide or the 2-dodecen-5-olide, or, respectively, the salt or the ester of the 5-hydroxy-2-decanoic acid or the 5-hydroxy-2-dodecanoic acid, will take place in a medium having a pH comprised between about 4.5 and 8.5, preferably comprised between about 6.5 and 7.0. The pH can be adjusted using a $NH_4OH$ solution, which has the advantage of satisfying the need of the microorganisms for nitrogen. If necessary, a buffer solution is added to the reaction medium to keep the pH at a constant value.

When the α,β-unsaturated 5-hydroxy acids, or, respectively, the corresponding salts, are used as starting product, there will be obtained, as a function of the chosen reaction conditions, in particular the pH, the salt of the saturated 5-hydroxy acid, the free acid, even the saturated lactone, or a mixture containing two or three of these products. At the end of the reaction, the crude product can be easily transformed into the lactones by an acidification of the solution which causes a spontaneous cyclization.

In case the esters of the α,β-unsaturated 5-hydroxy acids are used, the obtained saturated esters are saponified by the addition of an acid, and the above-mentioned cyclization is also observed.

The process of the present invention is elucidated in the following scheme for the particular case of the use of bacteria of the Clostridium genus:

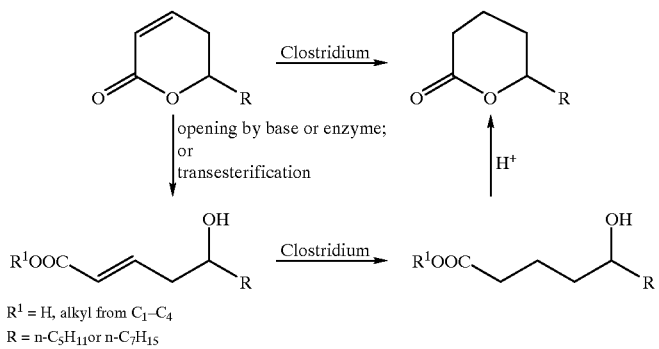

$R^1$ = H, alkyl from $C_1$–$C_4$
R = n-$C_5H_{11}$ or n-$C_7H_{15}$

In the prior art, there is not found any mention of the use of bacteriae of the Clostridium genus for the hydrogenation of 2-decen-5-olide or 2-dodecen-5-olide.

Furthermore, it has nowhere been disclosed or suggested to use bacteriae to hydrogenate 5-hydroxy-2-decanoic or 5-hydroxy-2-dodecanoic acid. In particular, the use of bacteriae of the Clostridium genus for this purpose is nowhere described or suggested. Now, we have discovered that according to the invention, it was possible to carry out successfully this biocatalytical reaction and, in particular, to obtain large productivity rates and high concentrations of the desired products, higher than those observed beforehand. This is an unexpected result. It is in effect well known that these lactones, which are components of the essential oil of the *Cryptocarya massoia* plant, are very probably the reason for the toxicity of this essential oil against a good number of microorganisms. The toxicity of these lactones has moreover been invoked as being the reason for the low conversion rates in the hydrogenation reaction of these lactones using the microorganisms described in the patent applications EP-A-425 001 and EP-A-577 463, even if the substrates 2-decen-5-olide et 2-dodecen-5-olide were employed in very low concentrations.

Surprisingly, we have now established that, according to the process of the invention, high concentrations of the unsaturated lactones can be used without intoxication of the microorganisms, resulting in conversion rates which are clearly higher than those obtained with the yeasts or fungi described in the prior art. It was even more surprising to find that bacteriae, in particular those used in the present invention are capable of reducing both the lactone (with the lactonic cycle being intact) and the corresponding α,β-unsaturated hydroxy acid or, respectively, its salt or ester (with the lactonic cycle being broken). The conversion rates were found to be of a similar order of magnitude in both cases. In view of the well-known effect that even minor changes in the structure of the substrate may have a paramount effect on the reactivity of the microorganism in microbiological reactions, the results obtained were totally unexpected.

By using the process of the invention, we could successfully obtain 5-decalactone and 5-dodecalactone in concentrations up to 13 g/l and volumetric productivities which can reach 1 g/lh.

The lactones can be used as such in the reaction of the invention, e.g. in the pure state or as found in Massoia extract. When it is preferred to use the substrates in form of the salt of the 5-hydroxy decenoic or 5-hydroxy dodecenoic acid, a convenient method to obtain these is the following.

The desired lactone is heated to 60° C. and then slowly titrated with a 30% NaOH solution until complete opening of the cycle. The thus-obtained sodium salt is then directly used for the bioconversion reaction.

According to a preferred embodiment of the reaction of the invention, it turned out to be advantageous to submit the bacteriae to a growth or culturing step before addition to the substrate.

In general, the culture medium for these bacteriae contains yeast extract, $(NH_4)_2SO_4$, $KH_2PO_4$, $MgSO_4$ and $FeSO_4$. It is sometimes necessary to add vitamins, like biotine or p-aminobenzoate. The temperature favorable for the growing process is comprised between 25° C. and 37° C. As carbon source, glucose can be used, which is held at a concentration comprised between about 5 and 50 g/l, preferably about 20 g/l, by the addition of a concentrated glucose solution. The sterility and the anaerobiosis of the system is maintained by using appropriate materials; in the beginning, the liquid and gaseous phases of the culture are purged with nitrogen. The reaction medium is stirred.

In a typical run, 4–5 ml of the culture medium of the microorganism was kept in culture tubes under anaerobic conditions at −40° C. One tube is unfrozen and used to inoculate a penicillin flask containing 50 ml of the medium. After 48 h of culturing, the inoculum can be used to seed a 2-litre bioreactor or two I-litre bottles containing 800 ml of the medium. These latter can themselves be used, after another 24 h of growth, to seed a bioreactor having a volume of 15 liters.

The culturing step can of course be omitted, which gives rise to a longer conversion time.

The biotransformation is terminated when the redox potential of the medium starts to grow rapidly, or when the evolution of the $H_2/CO_2$ mixture is no longer observed. The mixture is then acidified to a pH of 2–3. The product of the biotransformation is then isolated by traditional methods, for example by extraction, for which diisopropyl ether can be used. The emulsions formed by the abundance of biomass can be destroyed by centrifugation. As the ether also contains butyric acid produced by the Clostridium, it is washed with the solution of a mild base, for example an aqueous saturated $NaHCO_3$ solution. The solvent is dried with an appropriate agent, for example anhydrous sodium sulfate, then evaporated, and the remaining product is distilled. In this way, a product having a purity of 99% is obtained.

The invention will now be illustrated in greater detail by the following examples in which the temperatures are indicated in degrees centigrade and the abbreviations have the usual meaning in the art. Some examples were not carried out under optimum conditions, explaining the obtained low conversions. When the salt of the unsaturated 5-hydroxy acid was used as substrate, the crude product obtained after hydrogenation will always be referred to as 5-hydroxy-2-decanoic or 5-hydroxy-2-dodecanoic acid, although the product may also contain or being composed of the respective salt or lactone, as specified beforehand.

EMBODIMENTS OF THE INVENTION

EXAMPLE 1

5-Hydroxy-2-decenoic acid, in the form of a solution of its sodium salt, was added to a culture of *Clostridium tyrobutyricum* I-776 until a concentration of 0.5 g/l of said salt was reached. After 24 h, a conversion of 100% to 5-hydroxy-2-decanoic acid was observed.

EXAMPLE 2

The procedure described in Example 1 was repeated, with the exception that *Clostridium tyrobutyricum* I-775 was used. The conversion was 100%.

EXAMPLE 3

The procedure described in Example 1 was repeated, with the exception that *Clostridium tyrobutyricum* CNRZ 556 was used. The conversion was 100%.

EXAMPLE 4

The procedure described in Example 1 was repeated, with the exception that *Clostridium pasteurianum* DSM 525 was used. The conversion was 17%.

EXAMPLE 5

The procedure described in Example 1 was repeated, with the exception that *Clostridium beijerincki* DSM6422 was used. The conversion was 12.3%.

EXAMPLE 6

The procedure described in Example 1 was repeated, with the exception *Clostridium acetobutylicum* DSM 792 was used. The conversion was 6%.

EXAMPLE 7

A 2l bioreactor containing 1 l medium of pH 6 and 35° C. was seeded with an inoculum of 50 ml of *Clostridium tyrobutyricum* I-776. The mixture was stirred at 300/min, and strict anaerobic and sterile conditions were maintained. After several hours, when the culture started to grow, indicated by the evolution of gas from the solution, the medium was fed with the sodium salt of 5-hydroxy-2-decenoic acid. After 52 h, 5-hydroxy-decanoic acid was obtained in a concentration of 1.75 g/l, corresponding to a conversion of 27%. 8δDecalactone can be obtained by acidification of the primary product.

EXAMPLE 8

The procedure as described in Example 7 was repeated, with the exception that the medium had a pH of 7. The amount of 5-hydroxy-2-decanoic obtained was 4.95 g (conversion 99%), from which δ-decalactone can be obtained by acidification.

EXAMPLE 9

The procedure as described in Example 8 was repeated, with the sodium salt of 5-hydroxy-2-decanoic acid being replaced by the sodium salt of 5-hydroxy-2-dodecanoic acid. After 52h, 1.1 g/l of 5-hydroxy-2-dodecanoic acid, corresponding to a conversion of 57%, were obtained. The acid is transformed into δ-dodecalctone by acidification.

EXAMPLE 10

A 15 l bioreactor containing 10 l of medium was seeded with 2×800 ml of an inoculum of *Clostridium tyrobutyricum* I-776. Strict anaerobic and sterile conditions were maintained. The pH was kept at 6.5, the temperature at 35° C., the stirring speed at 300/min; the initial concentration of glucose was 90 g/l. When the glucose was exhausted (48 h), the cells were gathered for centrifugation over 30 min at 4° C., for example at 10000 ×g. The humid mass of the cells was gathered and put into a 2 l reactor under strictly sterile and anaerobic conditions. The volume was adjusted to a total of 1 l with a buffer solution of pH 7. The medium contained about 90 g/l of dry matter. $NH_4OH$ was added to maintain a pH of 7, and a glucose solution of 500 g/l was also added, to adjust the glucose concentration to about 20 g/l. 2-Decen-5-olide was added semicontinuously. After 40 h, δ-decalactone was obtained in a concentration of 7 g/l, which corresponds to a conversion of 72%.

EXAMPLE 11

The procedure as described in Example 10 was repeated, with the exception that the sodium salt of 5-hydroxy-2-decenoic acid was added. After 22 h, 13 g/l of 5-hydroxy-2-decanoic acid, corresponding to a conversion of 100%, were obtained. The acid can be converted into δ-decalactone by acidification.

EXAMPLE 12

A 15 l bioreactor containing 10 l of medium was seeded with 2×800 ml of an inoculum of *Clostridium tyrobutyricum* I-776 Strict anaerobic and sterile conditions were maintained. The pH was kept at 6.0, the temperature at 35° C., the stirring speed at 300/min; the initial concentration of glucose was 90 g/l. When the glucose was exhausted (48 h), the cells were gathered for centrifugation over 30 min at 4° C., for example at 10000 ×g . The humid mass of the cells was gathered and put into a 2 l reactor under strictly sterile and anaerobic conditions. The volume was adjusted to a total of 1 l with a buffer solution of pH 7. The medium contained about 90 g/l of dry matter. $NH_4OH$ was added to maintain a pH of 7, and a glucose solution of 500 g/l was also added, to adjust the glucose concentration to about 40 g/l. 2-Dodecen-5-olide was added semicontinuously. After 44 h, δ-dodecalctone was obtained in a concentration of 9.6 g/l, which corresponds to a conversion of 99%.

EXAMPLE 13

The procedure as described in Example 12 was repeated, with the exception that the sodium salt of 5-hydroxy-2-dodecenoic acid was added. After 52 h, 5.1 g/l of 5-hydroxy-2-dodecanoic acid, corresponding to a conversion of 78%, were obtained. The acid can be converted into δ-dodecalctone by acidification.

We claim:

1. Process for the preparation of δ-decalactone or δ-dodecalactone, comprising the hydrogenation of 2-decen-5-olide or 2-dodecen-5-olide, or a derivative thereof, by a bacteria of the Clostridium genus.

2. Process according to claim 1, wherein 2-decen-5-olide or 2-dodecen-5-olide is used in the hydrogenation reaction.

3. Process according to claim 1, wherein 5-hydroxy-2-decenoic acid or 5-hydroxy-2-dodecenoic acid, or a salt thereof, is used in the hydrogenation reaction.

4. Process according to claim 1, wherein the bacteria is selected from the group consisting of *Clostridium tyrobutyricum, Clostridium pasteurianium, Clostridium beijerincki, Clostridium acetobutylicum, Clostridium oceanium, Clostridium sticklandii,* and *Clostridium thermobutyricum.*

5. Process according to claim 4, wherein the bacteria is selected from the group consisting of the strains *Clostridium tyrobutyricum* I-775, *Clostridium tyrobutyricum* I-776, *Clostridium tyrobutyricum* CNRZ 556, *Clostridium pasteurianium* DSM 525, *Clostridium beijerincki* DSM 6422 and *Clostridium acetobutylicum* DSM 792.

6. Process according to claim 5, wherein the bacteria strain is *Clostridium tyrobutyricum* I-775, *Clostridium tyrobutyricum* I-776 or *Clostridium tyrobutyricum* CNRZ 556.

7. Process according to claim 3, wherein said salt of 5-hydroxy-2-decenoic acid or 5-hydroxy-2-dodecenoic acid is obtained by treating 2-decen-5-olide or 2-dodecen-5-olide with a base or an enzyme.

8. Process according to claim 1, wherein a $C_1$ to $C_4$ ester of 5-hydroxy-2-decenoic acid or of 5-hydroxy-2-dodecenoic acid is used in the hydrogenation reaction.

9. Process according to claim 1, wherein in the course of the hydrogenation reaction the pH is maintained at a value comprised between 4.5 and 8.5.

10. Process according to claim 9, wherein the pH is held at a value comprised between 6.5 and 7.0.

* * * * *

UNITED STATES PATENT AND TRADEMARK OFFICE
CERTIFICATE OF CORRECTION

PATENT NO.    : 6,025,170

DATED         : February 15, 2000

INVENTORS     : Gil BRETLER et al.

It is certified that error appears in the above-identified patent and that said Letters Patent is hereby corrected as shown below:

Column 2, line 39, after "Germany" and before the period at the end of the sentence, insert --,the most preferred being *Clostridium tyrobutyricum I-776, Clostridium tyrobutyricum I-775* and *Clostridium tyrobutyricum CNRZ556*--.

Signed and Sealed this

Twenty-seventh Day of March, 2001

Attest:

NICHOLAS P. GODICI

Attesting Officer

Acting Director of the United States Patent and Trademark Office